United States Patent [19]

Burgoyne

[11] Patent Number: 5,972,386
[45] Date of Patent: Oct. 26, 1999

[54] DRY SOLID MEDIUM FOR STORAGE AND ANALYSIS OF GENETIC MATERIAL

[75] Inventor: Leigh Alexander Burgoyne, Mitcham, Australia

[73] Assignee: Flinders Technologies Pty, Ltd., Australia

[21] Appl. No.: 08/574,888

[22] Filed: Dec. 19, 1995

[51] Int. Cl.[6] .............................. A61K 9/14; A61K 9/50; C12Q 1/68; C12P 19/34

[52] U.S. Cl. ......................... 424/488; 424/486; 424/488; 424/489; 424/502; 435/6; 435/91.2; 435/91.5; 435/91.51

[58] Field of Search .............................. 435/6, 91.2, 91.5, 435/91.51; 935/77; 424/488, 486, 489, 497, 502

[56] References Cited

U.S. PATENT DOCUMENTS

| Re. 35,716 | 1/1998 | Stapleton et al. | 435/3 |
|---|---|---|---|
| 3,418,079 | 12/1968 | Boehringer et al. | 23/253 |
| 4,455,370 | 6/1984 | Bartelsman et al. | 435/6 |
| 4,677,054 | 6/1987 | White et al. | 435/6 |
| 5,092,466 | 3/1992 | Anderson | 206/438 |
| 5,188,963 | 2/1993 | Stapleton | 435/299 |
| 5,281,516 | 1/1994 | Stapleton et al. | 435/3 |
| 5,346,672 | 9/1994 | Stapleton | 422/102 |
| 5,382,511 | 1/1995 | Stapleton | 435/6 |
| 5,413,924 | 5/1995 | Kosak et al. | 435/177 |
| 5,436,129 | 7/1995 | Stapleton | 435/6 |
| 5,451,500 | 9/1995 | Stapleton | 435/6 |
| 5,616,478 | 4/1997 | Chetverin et al. | 435/91.2 |

FOREIGN PATENT DOCUMENTS

| B 30256/84 | 1/1985 | Australia . |
|---|---|---|
| 0 130 523 A2 | 1/1985 | European Pat. Off. . |
| 0 221 308 A1 | 5/1987 | European Pat. Off. . |
| 0 261 955 A2 | 3/1988 | European Pat. Off. . |
| WO/90/03959 | 4/1990 | WIPO . |
| WO 91/107486 | 5/1991 | WIPO . |
| WO 93/07292 | 4/1993 | WIPO . |
| WO 93/19207 | 9/1993 | WIPO . |
| WO 94/26935 | 11/1994 | WIPO . |
| WO 96/11406 | 4/1996 | WIPO . |

OTHER PUBLICATIONS

M.Gross–Bellard, et al., "Isolation of High–Molecular–Weight DNA from Mammalian Cells", *Eur. J. Biochem.* 36:32–38 (Jul. 2, 1973).

Bruce E. Ames, et al., "Uric Acid Provides an Antioxidant Defense in Humans Against Oxidant–and Radical–Caused Aging and Cancer: A Hypothesis", *Proc. Natl. Acad. Sci. USA* 79(11):6858–6862 (Nov. 1981).

Leigh Burgoyne Ph.D., et al., "Safe Collection, Storage and Analysis of DNA From Blood", Abstract for Conference: 5th International Symposium on Human Identification, Oct. 8–11, 1994.

Declan Butler, "UK to set up DNA database of criminals . . . ", *Nature* 370(6491):588–589 (Aug. 1994).

(List continued on next page.)

*Primary Examiner*—Carla J. Myers
*Assistant Examiner*—Diana Johannsen
*Attorney, Agent, or Firm*—Merchant & Gould P.C.

[57] ABSTRACT

The present invention provides a dry solid medium for storing a sample of a genetic material, including RNA and DNA, in a form suitable for subsequent analysis. The dry solid medium of the invention includes a dry solid matrix and a composition including a protein denaturing agent, and a chelating agent. The dry solid medium can further include a component which functions in subsequent analysis of the genetic material using, for example, PCR, reverse transcriptase initiated PCR, LCR, RFLP, or genetic hybridization. A component for subsequent analysis includes, for example, a nucleotide sequences such as a primer, DNA or RNA probe, and a target sequence stabilizer. The dry solid medium can also include a retaining agent to enhance retention of a component for subsequent analysis. The invention also provides methods for using the dry solid medium of the invention. The dry solid media and methods of use thereof are particularly suited for use in automated systems.

17 Claims, 3 Drawing Sheets

OTHER PUBLICATIONS

P.T. Gilham, "The Synthesis of Polynucleotide–Celluloses and Their Use in the Fractionation of Polynucleotide", *J. American Chem. Soc.* 86:4982–55 (Oct.–Dec. 1964).

Peter Gill, et al., "Forensic Application of DNA 'Fingerprints'", *Nature* 318:577–79 (1985).

Michael A. Harvey, et al., "Impregnated 903 Blood Collection Paper: A Tool for DNA Preparation from Dried Blood Spots for PCR Application", 1995 (vol. #, p.# not applicable).

L. Jervis, et al., "Purification of Ribonuclease $T_1$ on Porous Glass Affinity Adsorbents", *J. of Chromotography* 97(1):33–38 (Oct. 1974).

Kwok–Wai Lam, et al., "Inhibition of Ascorbate Oxidation by Urate", *J. Inorganic Biochemistry*, 22(4):241–248 (1984).

Linda Madisen, et al., "DNA Banking: The Effects of Storage of Blood Isolated DNA on the Integrity of DNA", *American J. of Med. Gen.* 27(2):379–390 (1987).

T. Maniatis, et al., "Molecular Cloning—A Laboratory Manual" *Cold Spring Harbor Laboratory* Southern Transfer pp. 382–289, Preparations of Buffers and Solutions p. 447 (1982).

Stuart L. Marcus, "Purification of Avian Myeloblastosis Virus DNA Polymerase by Affinity Chromatography on Polycytidylate–Agarose", *J. of Virology* 14(4):853–859 (Oct. 1974).

Edward R.B. McCabe, et al., "DNA Microextraction from Dried Blood Spots on Filter Paper Blotters: Potential Application to Newborn Screening", *Hum. Gent*. 75(3):213–216 (Mar. 1987).

Mohindar S. Poonian, "Covalent Attachment of Nucleic Acids to Agarose for Affinity Chromatography", *Biochemistry* 10(3):424–427 (1971).

B. Singer, et al., *Biochemistry* 4(2):226–233 (Feb. 1965).

Patrick E. Williams, et al., "Evaluation of a Novel Matrix for the Analysis of DNA and Its Application to Automated DNA Sample Processing", Abstract for Conference: 5th International Symposium on Human Identification, (Oct. 8–11, 1994).

Declaration of Michael J. Kvasnik (w/Exhibits A–F), Dec. 1995 (vol.#, p#. not applicable).

Nancy R. Webb, et al., "Purification of the Messenger RNA Cap–Binding Protein Using New Affinity Medium", *Biochemistry* 23(2):177–181 (Jan. 1984).

International Search Report and Annex to International Search Report for International Application No. PCT/AU 89/00430.

Promotional Letter from Schleicher & Schuell, dated Jul. 31, 1995.

"UltraPAK® Customized DNA Collection Systems" brochure, 1993 (vol.#, p.# not applicable).

"UlstraSTAIN® Blood Storage System", brochure, 1993 (vol.#,p# not applicable).

SEQUENCE LISTING

```
(1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 23 base pairs
       (B) TYPE: nucleic acid
```

```
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

TGACTGAGTA CAAACTGGTG GTG                                                     23

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

CTCTATGGTG GGATCATATT CA                                                      22

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

TGGGCTGGAA TGGAAAGGAA TGCAAAC                                                 27

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:
```

(vi) ORIGINAL SOURCE:

(xi) SEQUENCE DESCRIPTION: SEQ ID NO:4:

TCCATTCGAT TCCATTTTTT TCGAGAA                                           27

(2) INFORMATION FOR SEQ ID NO:5:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

GAATGTATTA GAATGTAATG AACTTTA                                           27

(2) INFORMATION FOR SEQ ID NO:6:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

TTCCATTCCA TTCCATTCCT TTCCTTT                                           27

(2) INFORMATION FOR SEQ ID NO:7:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

GTGCTGCAGG TGTAAACTTG TACCAG                                            26

(2) INFORMATION FOR SEQ ID NO:8:

(i) SEQUENCE CHARACTERISTICS:
          (A) LENGTH: 28 base pairs

```
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

CACGGATCCG GTAGCAGCGG TAGAGTTC                                          28
```

DRY SOLID MEDIUM FOR STORAGE AND ANALYSIS OF GENETIC MATERIAL

RELATED TECHNOLOGY

The reader is advised of technology related to the present invention which is disclosed in U.S. patent applications Ser. No. 08/480,135, U.S. Pat. No. 5,756,126, 08/320,041, abandoned, and Ser. No. 08/159,104, U.S. Pat. No. 5,496, 562. U.S. Ser. No. 08/480,135, U.S. Pat. No. 5,756,126, and 08/320,041, abandoned, are continuation-in-part applications of U.S. Ser. No. 08/159,104, U.S. Pat. No. 5,496,562. The disclosures of U.S. Ser. No. 08/480,135, U.S. Pat. No. 5,756,126, 08/159,104, U.S. Pat. No. 5,496,562, and 08/320, 041, abandoned, are incorporated herein by reference.

FIELD OF THE INVENTION

The field of the present invention pertains to a dry solid medium and method for collection of genetic material in a form suitable for storage or subsequent analysis. The invention further provides for analysis of stored genetic material including methods suited for automated analyzing systems.

BACKGROUND

Blood containing genetic material (including DNA or RNA) to be analyzed has typically been transported from the place of removal, from a human or animal, to the place of analysis as purified genetic material, liquid whole blood, frozen whole blood or whole blood dried onto paper. However, all of these methods have disadvantages. Transport of genetic material in blood as dried, purified genetic material is most desirable, but it requires a high standard of technical assistance to be available at the place of removal from the human or animal. When technical assistance is not available at the place of removal, whole blood or other unpurified samples are usually sent to a central facility where the genetic material is purified.

Transport of liquid whole blood often involves the need for sterility of collection. Under some circumstances, this is extremely inconvenient, for example, where the sample is a heel-prick taken from an infant. The transport of liquid whole blood or frozen blood may also require temperature controlled transport or a transport system other than the regular postal system. This is true even before considering public health concerns. In addition, concern over pathogens associated with whole blood, such as the HIV virus, generally rule out the transport of a potentially infectious liquid or frozen sample except under proper and expensive supervision.

Transport of blood dried on filter paper is a proven alternative to the above procedures. Genetic material can be extracted and isolated from whole blood spots which are dried on filter paper, in a form and in sufficient quantities for use in genetic analysis. McCabe, E. R. B., et al., "DNA Microextraction From Blood Spots on Filter Paper Blotters: Potential Screening Applications to Newborn Screening," Hum. Genet. 75:213–216 (1987). However, the procedure still suffers from a number of disadvantages. For example, typically, there has been no deliberate and rapid destruction of blood associated microorganisms. The presence of pathogenic microorganisms may create a potential hazard for blood handling personnel. Moreover, some microorganisms may cause damage to the genetic material. While some inhibition of microorganisms may occur through desiccation, it is known that slow desiccation, or even a small degree of rehydration under conditions of high relative humidity, may allow the growth of DNA or RNA destroying microflora.

Another disadvantage of present methods for dry transport of genetic material in blood is a lack of deliberate inhibition of processes which degrade genetic material. Hence, even in the presence of a bacteriostatic agent there are conditions that permit enzymatic, nonenzymatic and autolytic breakdown of the genetic material. Furthermore, using presently available methods of dry storage, considerable difficulty is encountered if desorption of high molecular weight DNA or RNA is required. The surface adsorption affects can cause loss of genetic material which may cause the preferential loss of the least degraded, i.e., the most desired class of DNA or RNA molecules.

Thus, there is a need for a safe, convenient and minimally labor intensive means for storage of a genetic material which is contained in a liquid sample.

However, even if a sample of genetic material is collected in a safe, convenient and reliable form for storage, subsequent analysis of the stored sample may give rise to logistic problems. This is especially true when there are many different types of analyses to be performed on a collected sample. The logistics tend to become even more complex when multiple samples are submitted for analysis.

For example, some methods of analysis of genetic material for a specific genetic sequence, such as polymerase chain reaction (PCR) analysis, require use of an oligonucleotide primer-pair. Generally a different primer-pair is used for each sequence analysis to be performed. And, because there are an extremely large number of possible primer pairs (for example, one for each sequence within the genes of humans, animals and all other living organisms including the pathogens of humans and animals), multiple sequence analyses in a single sample may give rise to immense logistic problems. The problems are potentially greater when multiple samples of genetic material are received for analysis, such as at a centralized analyzing facility.

Automated analysis of genetic material provides enhanced efficiency for processing large numbers of samples. However, automated analysis of a sample of genetic material still requires the automated system to have separate delivery devices for each different set of primers to prevent the occurrence of cross-contamination. Therefore, the range of genetic sequence analyses which can be performed at one time may be restricted due to the inherent problem of cross contamination of primers. Hence, there is a need for reducing the restrictions against analyzing multiple sequences or multiple samples of genetic material using automated systems.

SUMMARY OF THE INVENTION

The present invention provides a safe, convenient and minimally labor intensive apparatus and method for storage or analysis of a genetic material contained in a liquid medium. The invention further provides for storage of genetic material in such a way as to allow for simplified analysis of one or more samples of genetic material using automated systems.

The invention includes a dry solid medium for storage of a sample of genetic material. The dry solid medium of the invention is composed of a solid matrix and a composition which when applied to the dry solid medium protects against degradation of genetic material stored on the dry solid medium. The dry solid medium may further provide inactivation of microorganisms, including those which may be pathogenic to humans.

The composition of the dry solid medium may include a weak base, a chelating agent and a protein denaturant such as a detergent. In another embodiment, if long-term storage of a sample of genetic material is desired, the composition may further include a free radical trap.

According to the invention, genetic material stored on the dry solid medium may be analyzed using methods known in the art, for example, polymerase chain reaction (PCR), ligase chain reaction (LCR), reverse transcriptase initiated PCR, DNA or RNA hybridization techniques including restriction fragment length polymorphism (RFLP) and other techniques using genetic or DNA or RNA probes, genomic sequencing, enzymic assays, affinity labeling, methods of detection using labels or antibodies and other similar methods.

Genetic material stored on the dry solid medium of the invention may be analyzed in situ or after removal from the dry solid medium.

In another embodiment of the invention, the dry solid medium of the invention may include a component which is functional in subsequent analysis of the stored sample of genetic material. According to this embodiment, a component for subsequent analysis includes, for example, nucleotide sequences such as PCR primers, target sequence stabilizers, genetic probes, primers for genetic sequencing or sets of oligonucleotide substrates for LCR analysis. As disclosed herein, the compound for subsequent analysis may also include a suitably stable enzyme.

The invention also provides methods for using the dry solid medium. In one embodiment, the invention provides for storing a sample of genetic material on the dry solid medium in a substantially nondegraded form. The invention further provides a method for storage and subsequent analysis of a stored sample of genetic material. In a preferred embodiment, prior to analysis, the stored genetic material may be washed to remove compounds which may be associated with a sample of genetic material and which may inhibit subsequent analysis. Such compounds include, for example, protein, hemoglobin and components of the composition of the dry solid medium. The invention provides for the stored genetic material to be washed using an aqueous or a nonaqueous wash system.

The aqueous or nonaqueous wash system used to wash a sample of genetic material preferably provide for removing compounds which may inhibit subsequent analysis, without substantially affecting the stored genetic material or a component for subsequent analysis which may be included on the dry solid medium. Moreover, the aqueous and nonaqueous wash systems of the invention may also be used to wash genetic material which is stored, for example, on a solid matrix which does not have sorbed to it the composition of the invention.

In one embodiment, the nonaqueous wash system of the invention provides for contacting a sample of genetic material stored on the dry solid medium of the invention with a herein described single phase phenol solution. The single phase phenol solution is removed and the dry solid medium containing a sample of genetic material is subsequently contacted with an aqueous alcohol wash solution. The aqueous alcohol wash solution is removed and the sample of genetic material may further be washed with an aqueous ionic solution. The washed sample of genetic material may then be analyzed by methods known in the art, including those mentioned above.

Aqueous wash systems are known in the art. Under some circumstances, a wash system may cause some loss of a component for subsequent analysis which may be included on the dry solid medium of the invention. In one embodiment of the invention, a herein disclosed retaining agent may be used to reduce loss of a component for subsequent analysis during processing of the sample of genetic material.

A sample of genetic material stored on a dry solid medium of the invention may also be analyzed using standard enzymic tests used, for example, to detect phenylketonuria (PKU) or galactosemia, preferably after neutralizing the effects of protein denaturing components of the dry solid medium using, for example, a herein disclosed converter solution.

The dry solid medium and the dry solid medium including a component for subsequent analysis are particularly useful for analysis of a sample of genetic material using automated systems.

DETAILED DESCRIPTION OF THE INVENTION

Figure 1:
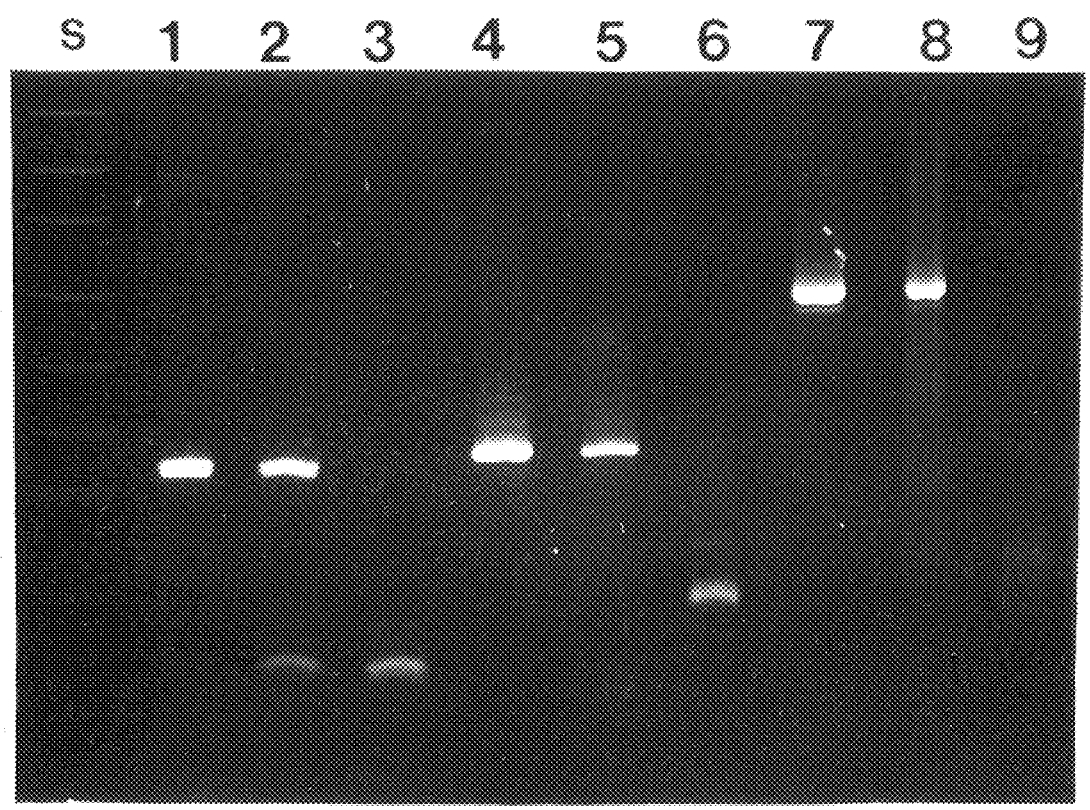
FIG. 1, Photograph of ethidium bromide stained gel of PCR amplified DNA from blood samples stored on a dry solid medium of the invention.

The present invention provides a dry solid medium for collection of genetic material in a form suitable for storage or subsequent analysis. The invention further provides methods for subsequent analysis of the genetic material collected on the dry solid medium of the invention. The dry solid medium and methods of use, disclosed herein, generally provide a safe, convenient and reliable storage medium for samples of genetic material which allows for accurate analytical results. Moreover, the invention further provides for enhanced analytical efficiency when multiple samples are analyzed using automated systems, for example, at a centralized analyzing facility.

In several places throughout the present specification guidance is provided through lists of examples. The inventor wishes to make clear that in each instance, the recited list serves only as a representative group. It is not meant, however, that the listed examples are exclusive.

As used herein, the phrase "genetic material" (GM) means either or both deoxyribonucleic acid (DNA) or ribonucleic acid (RNA). According to the invention, a sample of GM is collected on a dry solid medium of the invention by removing the sample from a source and applying the sample to a herein described dry solid medium. Methods for removing a sample of genetic material from a source are known in the art. For example, a sample of genetic material in blood may be removed from a human or animal source by venipuncture and the removed sample then applied to the dry solid medium of the invention.

As used herein a "sample of genetic material" or "sample of GM" includes a liquid having dissolved, suspended, mixed or otherwise contained therein, either or both DNA or RNA, cells which contain either or both DNA or RNA or cell components which contain either or both DNA or RNA. Once the sample of GM is applied to a dry solid medium, the liquid tends to evaporate (evaporation may be enhanced by drying methods known in the art, for example, a warm air dryer) leaving the DNA or RNA entrained to the dry solid medium in a dry form. The GM entrained to the dry solid medium in "dry form" may be purified DNA or RNA, semipurified DNA or RNA or DNA or RNA in cells.

The sample of GM which is applied to a dry solid medium may be derived from any source. This includes, for example, physiological/pathological body liquids (e.g., secretions, excretions, exudates and transudates) or cell suspensions (e.g., blood, lymph, synovial fluid, semen, saliva containing buccal cells, skin scrapings, hair root cells, etc.) of humans and animals; physiological/pathological liquids or cell suspensions of plants; liquid products, extracts or suspensions of bacteria, fungi, plasmids, viruses etc.; liquid products, extracts or suspensions of parasites including helminths, protozoas, spirochetes, etc.; liquid extracts or homogenates of human or animal body tissues (e.g., bone, liver, kidney, etc.); media from DNA or RNA synthesis; mixtures of chemically or biochemically synthesized DNA or RNA; and any other source in which DNA or RNA is or can be in a liquid medium.

A dry solid medium of the invention provides for storage or subsequent analysis of a sample of GM. A dry solid medium is composed of a solid matrix having sorbed thereto a composition which can protect against degradation of the GM stored on the medium. The composition may also cause inactivation of microorganisms. This includes microorganisms associated with a sample of GM which may potentially degrade the sample of GM or may be potentially pathogenic to human handlers of the stored sample of GM.

A dry solid medium and a composition sorbed to a solid matrix is disclosed in allowed U.S. patent application Ser. No. 08/159,104, U.S. Pat. No. 5,496,562, which is incorporated herein by reference.

As used herein, the term "storing", "storage", "stored" and other derivatives of the word "store" means the preservation of GM in a form suitable for subsequent analysis or which has not undergone substantial degradation. The time period for which GM may be stored according to the invention may be as short as the time necessary to transfer a sample of GM from a collection source to the place where subsequent analysis is to be performed. The conditions under which a sample of GM may be stored on a dry solid medium of the invention is variable. Typically, samples are stored at temperatures from −200° C. to 40° C. In addition, stored samples may optionally be stored in dry or desiccated conditions or under an inert atmosphere. Storage may be for a few seconds up to many years, preferably, about a few seconds up to 100 years.

In another embodiment of the invention, a dry solid medium may also include a component which is functional in a subsequent analysis to be performed on a stored sample of GM. Subsequent analysis which may be performed on a sample of GM stored on the dry solid medium include analysis methods known in the art, for example, polymerase chain reaction (PCR), ligase chain reaction (LCR), reverse transcriptase initiated PCR, DNA or RNA hybridization techniques including restriction fragment length polymorphism (RFLP) and other techniques using genetic probes (DNA or RNA), genomic sequencing, enzymatic assays, affinity labeling, methods of detection using labels or antibodies and other similar methods. In addition, the inventor recognizes that many new analytical and diagnostic methods may be developed in the future for which the dry solid medium and method of the invention may be suitable and which would fall within the spirit and scope of the claims appended hereto.

In the case of stored RNA, particularly unstable RNA, a component for subsequent analysis which may be included on a dry solid medium may provide protection against RNA degradation. Such a component includes RNase inhibitors and inactivators, genetic probes, complementary DNA or RNA (or functionally equivalent compounds), proteins and organic moieties that stabilize RNA or prevent its degradation.

Generally, a dry solid medium of the invention is also a suitable medium for storage of a component for subsequent analysis which may be included on the dry solid medium.

Once the GM has been collected on the dry solid medium, it may be encased in a protective material, for example, a plastic film, which may further protect against GM degradation during storage. Subsequent analysis of the GM stored on the solid medium of the invention may be performed in situ or, alternatively, the GM may first be removed from the dry solid medium prior to subsequent analysis.

I. THE DRY SOLID MEDIUM

A dry solid medium of the invention provides for entrainment of GM to the dry solid medium. As used herein the term "entrain", and derivatives thereof means that during storage the GM is bound to the dry solid medium without substantial reliance on ionic, covalent or van der waals interactions. As used herein, "without substantial reliance" means that such interaction may not be a significant factor in maintaining the GM on the dry solid medium. Preferably, ionic, covalent or van der waal interaction is not necessary for entrainment of GM to the dry solid medium.

A dry solid medium of the invention includes a composition sorbed to a solid matrix. As used herein, the term "sorb" means that the composition of the invention is absorbed, adsorbed or otherwise incorporated into or onto a solid matrix in such a way as not to be readily removed from the matrix unless subjected to conditions which are intentionally or inadvertently performed to remove the sorbed composition from the solid matrix. Preferably the sorbed composition is not readily removed under normal storage conditions.

A solid matrix suitable for a dry solid medium and method of the invention includes any material to which the composition will sorb and which does not inhibit storage or subsequent analysis of the GM applied to the dry solid medium. This includes a two-dimensional flat dry matrices or three-dimensional matrices such as a matrix combined with a binder to form a pellet or tablet to which the composition is sorbed.

In one preferred embodiment, the solid matrix is of a porous nature to provide entrainment of the GM onto the dry solid medium. A solid matrix suitable for this purpose includes, but is not limited to, a matrix which is cellulose based (e.g., cellulose, nitrocellulose or carboxymethylcellulose papers), hydrophilic polymers including synthetic hydrophilic polymers (e.g., polyester, polyamide, carbohydrate polymers), polytetrafluroethylene (Empore™, 3M, St. Paul, Minn.), fiberglass and porous ceramics.

According to the invention, GM may also be collected on a solid matrix which lacks the below-described composition of the invention. In addition, a component for subsequent analysis of a sample of GM may also be included on a solid matrix which lacks the composition of the invention. Furthermore, hemoglobin, protein or other compound associated with a sample of GM may be removed from a sample of GM stored on a solid matrix, which may or may not include a component for subsequent analysis of the stored GM, using the below described aqueous or nonaqueous extraction procedure. However, by using only a solid matrix for storage of GM, the GM degradation protection and microorganism inactivation effects of the composition of the invention may not be present.

To prepare a dry solid medium of the invention, a composition which protects against degradation of GM is sorbed to the solid matrix. As used herein, the phrase "protects against degradation of GM" means that a dry solid medium of the invention maintains the stored GM in a substantially nondegraded form. This provides a sample of GM suitable for many different types of subsequent analytical procedures. Protection against degradation of GM may include protection against substantial damaging of GM due to GM damaging events such as that caused by chemical or biological agents including action of bacteria, free radicals, nucleases, ultraviolet radiation, oxidizing agents, alkylating agents, or acidic agents (e.g., pollutants in the atmosphere).

The composition sorbed to the solid matrix of the invention may include one or more of a weak base, a chelating agent, or a protein denaturing agent such as a detergent or surfactant. In addition, the composition sorbed to the dry solid medium may also include a free radicle trap.

As used herein, a "free radical trap" is a compound which is sufficiently reactive to be preferred, over a DNA molecule or a component thereof, as a reactant with a free radical, and which is sufficiently stable not to generate damaging free radicals itself.

As used herein, a "weak base" suitable for the composition of the invention may be a Lewis base which has a pH of about 6 to 10, preferably about pH 8 to 9.5. One function of the weak base may be to act as a buffer to maintain a composition pH of about 6 to 10, preferably about pH 8.0 to 9.5, for example, pH 8.6. Hence, a weak base suitable for the composition of the invention may, in conjunction with other components of the composition, provide a composition pH of 6 to 10, preferably, about pH 8.0 to 9.5. Suitable weak bases according to the invention include organic and inorganic bases. Suitable inorganic weak bases include, for example, an alkali metal carbonate, bicarbonate, phosphate or borate (e.g., sodium, lithium, or potassium carbonate). Suitable organic weak bases include, for example, trishydroxymethyl amino methane (Tris), ethanolamine, triethanolamine and glycine and alkaline salts of organic acids (e.g., trisodium citrate). A preferred organic weak base is a weak monovalent organic base, for example, Tris. The weak base may be either a free base or a salt, for example, a carbonate salt.

Although the inventors do not wish to be limited to a single theory, it is believed that the weak base may provide a variety of functions, including protecting the GM from degradation. In addition to providing a buffer system, it is also believed that the weak base can act to ensure proper action of the below described chelating agent in binding metal ions. In addition, the weak base may also prevent the action of acid nucleases which may not be completely dependent on divalent metal ions for functioning.

The composition of the dry solid medium can also include a chelating agent. As used herein, a chelating agent is any compound capable of complexing multivalent ions including Group II and Group III multivalent metal ions and transition metal ions (eg., Cu, Fe, Zn, Mn, etc). According to the invention, a preferred chelating agent is a strong chelating agent such as to ethylene diamine tetraacetic acid (EDTA). Chelating agents such as a citrate or oxalate are also suitable for the invention. The chelating agent may be added to the composition simultaneous with application of a sample of GM to the dry solid medium.

Although the inventors do not wish to be limited to a particular theory, it is believed that one function of the chelating agent of the invention is to bind multivalent ions which if present with the stored GM may partake in causing damage to the GM. Ions which may be chelated by the chelating agent include multivalent active metal ions, for example, magnesium and calcium, and transition metal ions, for example, iron. Both calcium and magnesium are known to promote GM degradation by acting as co-factors for enzymes which may destroy GM (e.g., most known nucleases). In addition, transition metal ions, such as iron, may readily undergo oxidation and reduction and damage nucleic acids by the production of free radicals or by direct oxidation.

The composition of the dry solid medium can further include a protein denaturing agent. As used herein, a protein denaturing agent functions to denature non-GM compounds, for example, proteins, which are associated with the stored GM. If the protein denaturing agent is a detergent or a surfactant, the surfactant may also act as a wetting agent to facilitate the uptake of a sample by the dry solid medium. The terms "surfactant" and "detergent" are synonymous and may be used interchangeably throughout the specification. According to the invention, any agent which denatures proteins without substantially affecting a sample of GM may be suitable for the invention. Preferred protein denaturing agents include detergents. As used herein "detergents" include ionic detergents, preferably anionic detergents.

A preferred anionic detergent suitable for the invention may have a hydrocarbon moiety, such as an aliphatic or aromatic moiety, and one or more anionic groups. Particularly preferred anionic detergents include sodium dodecyl sulphate (SDS) and sodium lauryl sarcosinate (SLS).

In one preferred embodiment, the ionic detergent of the invention causes inactivation of a microorganism which has protein or lipid in its outer membranes or capsids, for example, fungi, bacteria or viruses. This includes microorganisms which may be pathogenic to humans or which may cause degradation of GM.

Although not wishing to be limited to a single theory, it is believed that inactivation of a microorganism by a detergent is a result of destruction of the secondary structure of the organisms external proteins, internal proteins, protein containing membranes, or any other protein necessary for viability. The inventor recognizes that the detergent may not inactivate some forms of organisms, for example, highly resistant bacterial spores and extremely stable enteric virions. Moreover, the inventor further recognizes that while it may be desirable to inactivate a microorganism, the GM of a microorganism, either associated with the stored sample of GM or not, is also amenable for storage or subsequent analysis on the dry solid medium of the invention.

The composition of the invention may optionally include a free radical trap. A free radical trap according to the invention is defined above. Examples of a suitable free radical trap includes: uric acid or a urate salt, mannitol, benzoate (Na, K, Li or tris salt), 1–3 dimethyl uric acid, guanidine, guanine, thymine, adenine, cytosine, N-acetyl-histidine, histidine, deferoxamine, dimethyl sulfoxide, 5'5' dimethyl pyrroline-N-oxide, thiocyanate salt and thiourea. Preferred free radical traps include mannitol, thiocyanate salts, uric acid or a urate salt. According to the invention, the longer the period of time for which the GM is to be stored the more likely that a free radical trap may be advantageously included in the composition sorbed to the solid matrix. However, even if the GM is only to be stored for a matter of minutes, a free radical trap may still be incorporated into the composition.

While the inventor does not wish to be limited to any single theory, it is believed that one function of the free radical trap may be to trap GM damaging free radicals. For example, when the free radical trap used is uric acid or urate salt it may be converted to allantoin which may also act as a free radical trap that preferentially accepts free radicals that would otherwise damage nucleotide bases, for example, guanine.

Preferably, the free radical trap reacts with free radicals regardless of source (including free radicals present in the air). Free radicals may be generated through oxidation or reduction of iron in blood. Typically, free radicals are believed to be generated by spontaneous oxidation of the groups which are present, for example, in denatured serum protein of blood. Free radicals may also be generated by radiation such as UV light, x-rays and high-energy particles.

In addition, free radical traps which are also a weak acid, e.g. uric acid, may also function as a component of the buffering system provided by the weak base discussed above. Also, as in the case of uric acid or a urate salt, the free radical trap may act as an erodible surface because it is sparingly soluble such that a GM sample dried onto its crystals will be released as the urate beneath erodes. Hence, components of the composition, such as the free radical trap may enhance removal of a stored sample of GM if in situ processing is not desired.

Furthermore, after the sample of GM is applied to a dry solid medium, the dry solid medium with the applied sample of GM may be encased in a protective material, for example, a plastic film, which may further protect against degradation of stored GM. Examples of plastic films which are suitable according to the invention include polystyrene, polyethylene, polypropylene and other lamination plastics. Encasing the dry solid medium in a protective material may be accomplished by methods known in the art.

One simple method for encasing the dry solid medium in a plastic film is to put a dry solid medium into a container, e.g., a polyethylene bag, which is of sufficient size to hold the dry solid medium such that when a plastic film in liquid form is added to the container all parts of the dry solid medium will be coated by the liquid. The plastic film, in liquid form, is added to the container to coat the dry solid medium. The liquid plastic film is allowed to dry to provide a plastic film coating which encases the dry solid medium. Prior to analysis, the plastic film is removed from the dry solid medium using methods known in the art, for example, dissolving with organic solvents such as chloroform or mechanical stripping.

The inventors further note that a dry solid medium including components for subsequent analysis (discussed below), with an applied sample of GM, may also be encased in a protective material as described above.

II. SUBSEQUENT ANALYSIS OF GENETIC MATERIAL STORED ON THE DRY SOLID MEDIUM

As used herein, "subsequent analysis" includes any analysis which may be performed on a sample of GM stored on a dry solid medium of the invention. The GM stored on a dry solid medium may be analyzed in vitro. Alternatively, the GM may be removed from the dry solid medium prior to analysis. The sample of GM may be subjected to chemical, biochemical or biological analysis. Examples of subsequent analysis which may be performed on samples of GM stored on the dry solid medium include polymerase chain reaction (PCR), ligase chain reaction (LCR), reverse transcriptase initiated PCR, DNA or RNA hybridization techniques including restriction fragment length polymorphism (RFLP) and other techniques using genetic probes, genomic sequencing, enzymatic assays, affinity labeling, methods of detection using labels or antibodies and other similar methods.

In addition, diagnostic procedures presently performed on whole blood samples, for example, the Guthrie test for phenyl-ketonuria (PKU) or enzymatic tests, for example, galactosemia may be performed on blood samples stored on a dry solid medium of the invention after first neutralizing the affects of protein denaturing components of the dry solid medium, for example, using a "converter solution."An example of a converter solution is disclosed in Example 5.

GM stored on a dry solid medium of the invention may serve as a template for subsequent analysis of the GM using PCR methods. This includes PCR using DNA or RNA as a template. When RNA is the GM to be analyzed, the RNA may serve as a template using reverse transcriptase initiated PCR. The DNA sequence produced from the RNA template may then serve as a template for further PCR amplification.

Compounds associated with a stored sample of GM, including hemoglobin, protein or components of the composition of the dry solid medium, may interfere with subsequent analysis of a sample of GM stored on the dry solid medium. Preferably, such interfering compounds are substantially removed from the dry solid medium prior to subsequent analysis. If, for example, the sample of stored GM is in whole blood, prior to analysis by PCR, LCR, RFLP, reverse transcriptase initiated PCR, genetic probing or other technique, preferably, hemoglobin or protein associated with the GM stored on the dry solid medium is preferably removed. Hemoglobin or protein associated with the GM may be removed using, for example, aqueous or nonaqueous extraction procedures. In addition, an interfering compound which is a component of the composition of the invention (e.g., an ionic detergent) may be removed, using aqueous or nonaqueous extraction procedures or the herein disclosed converter solution, prior to subsequent analysis.

In one preferred embodiment, hemoglobin, blood protein or other protein associated with a sample of GM may be removed using nonaqueous extraction procedures, for example, the below-described single phase phenol wash method. In addition, the single phase phenol wash may be followed with the below-described ionic aqueous alcohol wash to provide ions necessary for subsequent PCR, LCR or similar analysis of GM stored on the dry solid medium. Methods for PCR, LCR, reverse transcriptase initiated PCR, DNA or RNA hybridization, genomic sequencing, and other methods of subsequent analysis are known in the art.

In another embodiment of the invention, a sample of GM associated with protein or hemoglobin which is stored on a dry solid medium of the invention may be removed using aqueous extraction. One such aqueous extraction procedure, for example, uses aqueous SDS and mercaptoethanol. According to this procedure, the sample of GM stored on the dry solid medium, with or without components for subsequent analysis, is washed with an alkaline solution of aqueous 6% SDS at pH 8.5 to 9.0 which contains a thiol, for example, 20 mM 2-mercaptoethanol or dithiothreitol. Another such aqueous extraction procedure, for example, uses pure water. The GM is then washed with iso-propanol to remove substantially all water, remaining impurities, and unwanted components (e.g., the iso-propanol wash may be accomplished using the aqueous alcohol wash solution described below for the single phase phenol wash).

As will be apparent to those skilled in the art, in situ subsequent analysis of GM stored on a dry solid medium of the invention with or without components for subsequent analysis may be of particular benefit in automated systems. As used herein, an "automated system" includes an "automatic fluid delivery system." According to the invention, an "automatic fluid delivery system" includes hand-held and robotic fluid delivery systems. Typically, an automatic fluid delivery system is a device which dispenses and removes fluid reagents to and from individual wells of multi-well reaction plates. A hand-held automatic fluid delivery system comprises a single plunger handle with multiple fluid aspirating and dispensing ends to simultaneously aspirate and dispense fluid of a fluid reaction system from single or multiple fluid reaction wells simultaneously. Robotic automatic fluid delivery systems are computer operated rather than hand-held and include such products as, for example, BIOMEK 2000 (Beckman Instruments, Fullerton, Calif.), Zymark Benchmate (Zymark, Hopkinton, Mass.) and ROSYS PLATO, Rapperswil, Switzerland. Automatic fluid delivery systems are also discussed in U.S. Ser. No. 08/320, 041 which is incorporated herein by reference.

A. SINGLE PHASE PHENOL WASH

Another aspect of the present invention provides an organic extraction method for removing hemoglobin or protein associated with a stored sample of GM. According to the invention, hemoglobin or protein may be removed from a stored sample of GM using a single phase phenol wash. Preferably, the single phase phenol wash also removes components of the composition of the invention (e.g., the detergent). The single phase phenol wash is performed by contacting a single phase phenol solution with a dry solid medium having applied thereto a sample of GM. The single phase phenol wash is removed from the dry solid medium containing a sample of GM and the dry solid medium is then contacted with an aqueous alcohol wash. The aqueous alcohol wash is then removed. If the sample of GM is to be analyzed by PCR, LCR or other method which relies on ions, the sample of GM may then be contacted with an ionic aqueous alcohol wash prior to PCR analysis. A nonaqueous wash system such as the single phase phenol wash (described below) or an aqueous wash system (described above) may also be used to wash a sample of GM stored on a solid matrix lacking the composition of the invention and which may or may not include a component for subsequent analysis of the GM.

The single phase phenol wash provides for removing a protein, hemoglobin, or a component of the composition of the dry solid medium which may effect the subsequent treatment to be performed on the GM stored on the dry solid medium without effecting the stored GM. Unlike prior art methods, the present wash system does not require two phase separations (aqueous and organic phase) during processing and tends not to dissolve GM present in blood. The single phase phenol wash is also amenable to automated systems.

The single phase phenol wash is also disclosed in allowed U.S. patent application Ser. No. 08/159,104, U.S. Pat. No. 5,496,562, and co-pending Ser. No. 08/480,135, U.S. Pat. No. 5,756,126 and 08/320,041, abandoned. The wash includes two solutions, referred to below as "single phase phenol solution" (solution A) and "aqueous alcohol wash solution" (solution B). A third solution, "ionic aqueous alcohol wash solution" (solution C), may be used, after the single phase phenol wash if the sample of GM is to be analyzed using a method which requires additional ions, for example, PCR and LCR.

Solution A: The single phase phenol solution includes phenol and hydroxyquinoline saturated with Tris-acetate and mercaptoethanol. Preferably, 50 grams (gm) of phenol is combined with 120 milligram (mg) of 8-hydroxyquinoline saturated with 10 milliliter (ml) of 1.0 molar (M) Tris-acetate at pH 6.0 to 9.0, preferably pH 8.0, and 1.0 ml 2-mercaptoethanol. After saturation by shaking at a temperature of about 0° C. to 20° C., preferably 0° C. to 4° C., the aqueous phase is removed and discarded. (The inventor notes that the single phase phenol wash is believed to be saturated with Tris Acetate and mercaptoethanol at 4° C. However, at use temperature, which is typically greater than 4° C., the solution is not believed to be saturated.) Solution B: The aqueous alcohol wash solution utilizes any $C_2$–$C_5$ alcohol, such as isopropanol or n-propanol, or any other similar water miscible solvent combined with an acetate salt or similar organic soluble salt which provides a pH of about 7.0 to 9.0, preferably about pH 7.8. In a preferred embodiment 75% by volume isopropanol is combined with 25% by volume of 0.1M potassium acetate at a pH of about 7.8. Solution C: The ionic aqueous wash solution is a wash solution which provides appropriate ions, for example, magnesium, manganese, sodium, protamine, tris and similar ions which may be useful in a subsequent analysis procedure. For PCR analysis, magnesium is preferred. Accordingly, the ionic alcohol wash solution utilizes any $C_2$–$C_5$ alcohol, such as isopropanol and n-propanol, or any other similar water miscible solvent combined with an acetate salt or similar organic soluble salt which provides a pH of about 6.0 to 8.5, preferably about pH 7.8. In a preferred embodiment for magnesium ions, 75% by volume isopropanol is combined with 25% by volume of 0.01M magnesium acetate at a pH of about 7.5.

According to the invention, a sample of GM associated with hemoglobin or protein which is stored on the dry solid medium is contacted with solution A for about 15 minutes to about 3 hours, preferably about 1.5 to about 2 hours, at a temperature which is greater than 37° C., preferably about 45–65° C., more preferably about 50° C. The temperature at which the sample of GM is contacted with solution A is not critical if the dry solid medium of the invention does not also include a component for subsequent analysis, such as a primer, which is discussed below. The solution A is then removed. Preferably, the sample of GM is then quickly washed 1–4 times, for a few seconds each time with fresh solution A.

After removal of solution A, the sample of GM is washed, for a few seconds, 1–4 times with solution B. Preferably, the solution B washes are at about 10° C. to 25° C. If solution C is to be used, after solution B is removed, solution C is applied to the sample of GM for about 1–60 minutes, preferably about 30 minutes, at a temperature of about 10° C. to 25° C. The solution C is removed and the sample of GM on the dry solid medium is dried.

Generally, the single phase phenol wash of the invention provides a substantially protein or hemoglobin free GM that provides a very convenient starting point for a variety of analytical procedures based on nucleic acids. The use of the single phase phenol wash and ionic aqueous alcohol wash is further described in the Examples.

According to the invention, the single phase phenol wash may be used to provide a substantially protein or hemoglobin free sample of GM stored on any solid system. Moreover, as described below, the single phase phenol wash is of particular benefit when a solid storage system incorporates a component for subsequent analysis such as an oligonucleotide primer. Hence, the single phase phenol wash is useful to remove proteins or hemoglobin from a sample of GM stored on a dry solid medium regardless of whether or not the storage medium incorporates the GM protecting composition of the invention and regardless of whether or not the storage medium includes components necessary for subsequent analysis.

B. DRY SOLID MEDIUM INCLUDING COMPONENTS FOR SUBSEQUENT ANALYSIS OF GENETIC MATERIAL

In another embodiment of the invention, the dry solid medium of the invention may include a component for subsequent analysis of a stored sample of GM. As used herein, "subsequent analysis" means any analysis which may be performed on a sample of GM stored on the dry solid medium. This includes chemical, biochemical or biological analysis. Examples of subsequent analysis which may be performed on a sample of GM stored on a dry solid medium include PCR, LCR, reverse transcriptase initiated PCR, DNA or RNA hybridization techniques including RFLP and other techniques using genetic or DNA or RNA probes, genomic sequencing, enzymatic assays, affinity labeling, methods of detection using labels or antibodies and other methods known in the art.

As used herein, a "component for subsequent analysis" of a stored sample of GM includes a molecule, compound, reagent or other component which may be functional in analyzing, or preserving for analysis, a sample of GM, or analyzing some other component stored with the GM on the dry solid medium.

In some instances, subsequent analysis will involve an analytical method which is used to establish the absence or presence of a particular genetic sequence. The genetic sequence to be analyzed is termed a "target sequence." The target sequence or other region of a sample of genetic material may serve as a template for PCR amplification.

One or more components for subsequent analysis may be included on the dry solid medium. The component included on the dry solid medium is dependent on the type of analysis to be performed on the sample of GM. The advantage of including a component for subsequent analysis will be readily apparent in situations where large numbers of samples of GM are simultaneously analyzed using automated systems. A component for subsequent analysis which may be included on a dry solid medium include, for example, an ion, an enzyme and a nucleotide sequence.

As used herein, "nucleotide sequence" includes compounds such as a primer, (e.g., a PCR primer, a primer for reverse transcriptase initiated PCR), sets of oligonucleotide substrates for LCR, DNA or RNA probe, oligonucleotides used in genetic sequencing, and a target sequence stabilizer.

As used herein, a "primer" means one pair of oligonucleotides, each of which is capable of annealing to a complementary nucleic acid sequence in a sample of GM, and which are oriented so that each primer will prime the synthesis of a strand of DNA (or conceivably, a strand of RNA) containing a sequence complimentary to the other oligonucleotide. For some applications, it may be desirable that the sequence of the oligonucleotide and its complimentary sequence is predetermined. In other applications, the sequence may be unknown. A plurality of degenerate primers or primers with sequences predicted to bind to the complimentary sequence may be used. The primer-pair may be used to amplify a pair of complimentary sequences and the sequence between the two complimentary sequences of known or unknown size. In addition, the primer may be used to amplify a template that is initially double-stranded DNA or RNA, as well as single-stranded DNA or RNA. For a single-stranded template, it is understood that the sequence complementary to one of the oligonucleotides will be synthesized by elongation of the first primer as it is annealed to its complementary sequence.

Primers for PCR or for reverse transcriptase initiated PCR may be present as a primer-pair, as is usual, or there may be only one primer as may be the case with genomic-sequencing or some protocols for reverse transcriptase initiated PCR.

In another embodiment of the invention, a component for subsequent analysis may be a nucleotide sequence referred to as a "target sequence stabilizer." According to this embodiment, a "target sequence stabilizer" is a nucleotide sequence which is complimentary to an entire region of RNA or DNA which is to be analyzed. A target sequence stabilizer may provide enhanced storage of an unstable single strand RNA or DNA stored as a sample of GM on the dry solid medium. As is known in the art, many single strand RNAs are unstable and vulnerable to degradation by low levels of omnipresent RNases. However, the inventor believes that by including a target sequence stabilizer on the dry solid medium, the target sequence stabilizer will bind to the single strand RNA (or DNA) sample and the "hybrid" formed is less vulnerable to degradation. For example, it is known in the art that double-stranded RNA/DNA hybrids are highly resistant to the common RNAases. The RNA or DNA annealed to the target sequence stabilizer may then be further analyzed using methods known in the art, for example, LCR or combinations of LCR and reverse transcriptase initiated PCR. Therefore, according to the invention, a component for subsequent analysis includes a component which functions by providing for protection from degradation of a stored sample of GM, such as a target sequence stabilizer.

The inclusion of a component for subsequent analysis, such as a nucleotide sequence, provides a significant advantage for simplifying subsequent analysis of GM by, for example, automated PCR systems. In addition, inclusion of an appropriate nucleotide sequence may provide additional protection from degradation of GM material such as unstable RNA.

Other components for subsequent analysis which may be included on the dry solid medium of the invention are, for example, ions, genetic probes or oligonucleotide or polynucleotide sequences with labels of diverse types, and suitably stable enzymes such as thermo stable enzymes. Labels may include a fluorescent chemical group, radioactive isotope, chemical binding agent (e.g., biotin), antigens or enzymes.

The use of some wash systems for removal of protein or hemoglobin associated with a sample of GM stored on a dry solid medium which includes a component for subsequent analysis may cause some loss of a component. The inventor has found that use of the single phase phenol wash of the invention to remove protein or hemoglobin associated with a sample of GM on a dry solid medium which includes a nucleotide sequence, generally provides for reduced or insubstantial loss of the included nucleotide sequence. By "insubstantial loss" it is meant that the wash, when completed, has not caused sufficient loss of the component to inhibit subsequent analysis. In the case of a component primer, "insubstantial loss" means that the wash has not caused sufficient loss of primer to prevent PCR, LCR, reverse transcriptase initiated PCR, probing, etc. Hence, because both the nucleotide sequence and sample of GM remain entrained to the dry solid medium during the washing procedure, in situ processing is possible. One skilled in the art will readily recognize the advantage this provides for analysis of GM using automated systems.

The loss of a component for subsequent analysis during processing of a stored sample of GM may be advantageously overcome, in some wash systems, for example, aqueous wash systems, through the use of a retaining agent.

As used herein, a "retaining agent" is a compound to which a component for subsequent analysis may be added, mixed, suspended or otherwise associated with, to reduce loss of the component from the dry solid medium during processing. A preferred retaining agent provides enhanced retention of a component to the dry solid medium when subjected to conditions which would otherwise cause greater loss of the component from the dry solid medium. For example, a component for subsequent analysis whose concentration on the medium could be reduced by using a nonaqueous wash system may be combined with a retaining agent that enhances retention of the component on the dry solid medium during a nonaqueous extraction. A component for subsequent analysis whose concentration on the medium could be reduced by using an aqueous wash system may be mixed with a retaining agent which enhances retention of the component on the dry solid medium during an aqueous extraction.

In one embodiment, the invention provides a retaining agent which may be associated with a component for subsequent analysis when a sample of GM stored on the dry solid medium is to be processed using an aqueous wash system. A preferred retaining agent will generally decrease the loss of, for example, a nucleotide sequence, when protein or hemoglobin associated with a sample of GM stored on the dry solid medium is extracted using an aqueous wash system.

An example of a retaining agent for use with an aqueous wash system is a wax. Alternatively, the retaining agent may be a hydrophilic carrier suspended in a wax.

As used herein, a "wax" is an organic mixture or compound of high molecular weight which is solid at room temperature but liquifies at higher temperatures. Waxes include hydrocarbons, fatty acids, alcohols, esters, polymers, long chain amides, homologous silicon based compounds, and thermo-label resins.

In one preferred embodiment, a component for subsequent analysis, such as a nucleotide sequence or an ion, is mixed with a hydrophilic solid carrier and suspended in wax. Hydrophilic solid carriers include, for example, starch, colloidal cellulose, cotton thread, and similar compounds. The mixture of component and carrier may subsequently be suspended in a wax having a melting point at or below the temperature of which subsequent analysis will occur. For example, if the sample of GM is to be analyzed using a PCR methodology a wax melting point of 45° C.–110° C., preferably 65° C.–90° C., should be selected. A preferred wax, according to the invention, is paraffin.

The wax suspension is allowed to solidify and the solid suspension deposited in small buttons or drops onto the dry solid medium. If a primer is the component mixed with the wax suspension, each drop preferably contains sufficient primer for a single PCR amplification. Hence, as will be described infra multiple drops for multiple samples of GM may be placed on a single dry solid medium card.

Although the inventor does not wish to be limited to a single theory, it is believed that during the aqueous system washing, the wax reduces the loss of the component to be retained. When, for example, the sample of GM is analyzed using PCR methodology, the temperature rise during the first PCR cycle causes the wax to melt, thus releasing the component, such as a primer, to initiate the reaction.

In another example of a retaining agent for an aqueous wash system, a component for subsequent analysis may be added to a cotton thread carrier and coated or impregnated with wax. For example, a cotton thread could be drawn through a trough of an aqueous soluble component for subsequent analysis. The thread could then be drawn through a drying chamber followed by a trough containing hot wax. Rolls of the wax-coated thread could be stored and subsequently cut into micro sections and heat stamped onto a dry solid medium to provide a component for subsequent analysis on a cotton thread suspended in wax.

In another embodiment, a component for subsequent analysis may be mixed with a wax without a hydrophilic carrier and applied to a dry solid medium using xerography methodology. According to this embodiment, a component for subsequent analysis may be deposited onto the dry solid medium in a water-insoluble retaining agent that becomes water soluble with the application of heat in the presence of water. Therefore, the component for subsequent analysis may be mixed into a wax and can be protected as a micro inclusion until the wax melts in water. Preferably, the wax containing a component for subsequent analysis are deposited onto predetermined locations on the dry solid medium. One example of this embodiment, is to apply hot, very dry wax dust containing a component for subsequent analysis onto the surface of the dry solid medium, similar to xerography processes.

In another embodiment of the invention, a retaining agent may be soluble in a wax using a hydrophilic liquid carrier. For example, a nucleotide sequence may first be made soluble in wax by complexing with a detergent. Preferred detergents are cationic detergents such as cetyltrimethyl ammonium bromide (CTAB). The detergent solubilized component is then mixed with wax and applied to the dry solid medium as described above.

Hence, the use of a retaining agent, under certain conditions used to process a sample of GM, may enhance retention of a component for subsequent analysis, thus yielding improved analytical results.

The advantage of including a component for subsequent analysis on the dry solid medium of the invention is readily seen in the case of PCR amplification of multiple samples using an automatic fluid delving system. For example, by including a primer necessary for amplifying a specific DNA or RNA gene sequence, multiple samples containing different primers may be analyzed using a single PCR reaction mixture. Typically, only one mixture of PCR enzyme and nucleotides to all vials is necessary. Moreover, even if different primers included with different GM samples require variation in reaction conditions such as magnesium ions and/or pH, these variations can be accommodated with only two additional pump or pipette systems to deliver inexpensive salts and buffers that will cover most contingencies.

A component for subsequent analysis is preferably included on the dry solid medium prior to processing a sample of GM stored on the medium. Various permutations for inclusion of the components is possible. For example, the component may be added to the composition of the dry solid medium prior to application of the composition to the solid matrix. Or, the components may be added to the solid matrix simultaneously with the composition. Alternatively, the composition of the invention may be applied to the solid matrix and the components applied subsequently. Foreseeably, a sample of GM may be applied to a dry solid medium and a component for subsequent analysis applied to the dry solid medium after collection of the sample of GM but before processing the sample of GM. It is also foreseeable that a component may be added to a dry solid medium after removing protein and/or hemoglobin but before subsequent analysis.

Thus, the invention provides for novel and previously impractical strategies to be made feasible by a dry solid medium including a component for subsequent analysis in combination with methods that allow for co-processing the component with the stored GM.

C. INCLUSION OF MULTIPLE NUCLEOTIDE SEQUENCES ON A SINGLE DRY SOLID MEDIUM

The dry solid medium of the invention may also be identified or referred to as a card. A card may be prepared in such a manner as to provide different component for subsequent analysis at different locations on a single card. When, for example, the component for subsequent analysis is a nucleotide sequence, multiple different nucleotide sequences for priming PCR amplification or stabilizing different target sequences may be included on one card.

As used herein, "multiple" means greater than one. A single sample of GM to be analyzed may be stored on a single card which is about 1 mm to 5 mm square. Therefore, a card which is about 5 cm×10 cm could be divided, for example, into 200 individual samples. Each individual 5 mm square could hold a different nucleotide sequence. Accordingly, a single 5 cm×10 cm card could provide for subsequent analysis of 200 different target sequences.

A dry solid medium card provides for analysis of multiple regions of GM from one collected sample. The cards may be pre-made, pre-labelled and stored for future use. In one preferred embodiment, a nucleotide sequence included on a card for subsequent analysis may be a primer. According to this embodiment, all or many of the primers for a particular application may be included on a single card. For example, one application may be to screen for multiple target sequences, in a single GM sample, which together characterize a particular genetic disease. Alternatively, a single card may contain primers to screen for the genomes of multiple viral diseases. Hence, these cards, including components for subsequent analysis, may be prepared, labelled and packaged for particular categories of usage, for example, penitentiary purposes (e.g., individual identification), insurance company screening and medical diagnosis of genetic diseases.

Moreover, the inclusion of, for example, a nucleotide sequence, allows the dry solid medium to be employed in different fields and still be conveniently processed together at one centralized, unspecialized center for automated analysis. This will allow the automated system to use one basal mixture of enzyme, and possibly buffer, to simultaneously amplify all target sequences for which primers are present on one type of card. As previously noted, the potential variations in ions and pH can be handled through a variety of ways, for example, separate delivery pumps. Alternatively, the use of a retaining agent may provide for individualized delivery of ions or other components used in subsequent analysis under varied conditions.

The following Examples are designed to teach those skilled in the art how to practice the invention. They are not intended to define or limit the scope of the invention in any way.

D. DRY SOLID MEDIUM KIT

The present invention also provides a kit for applying, storing or processing a sample of GM. A kit may include a dry solid medium and a container suitable for containing a dry solid medium during applying, storing or processing a sample of GM. According to this aspect of the invention, the kit may include one or more containers. An example of more than one container which is suitable for a kit includes a 96 well plate, as described below. The kit may also include one or more of any of the dry solid media disclosed herein. This includes a dry solid medium with or without a component for subsequent analysis and with or without a retaining agent. A dry solid medium included in a container may be freely removable from the container or fixed within the container.

The container of the kit may be any container suitable for use during application of a sample of GM to the dry solid medium or during application and one or more phases of subsequent processing of a sample of GM. Therefore, a kit may be used to apply a sample of GM to a dry solid medium and the dry solid medium removed from the kit container for processing in a different container. Alternatively, a sample of GM may be applied, stored, and processed all in the kit container.

One particularly useful aspect of a kit of the invention provides for transfer of a liquid sample of GM from an original collection container (such as a blood tube) to a dry solid medium of the kit without human contact. Hence, for example, using a robotic system such as a PLATO 3300 II (Rosys, Rapperswil, Switzerland) a sample of whole blood can be removed from an original collection container and transferred to a dry solid medium without need for human contact with the blood until after it is dried on the dry solid medium. If the robotic system has tracking capability, multiple samples of GM may be simultaneously transferred and tracked from original collection container onto dry solid medium in kit containers. For example, using a tracking system in which a bar code is placed on a collection container and a bar code reader is present on the robotic system, the location of a sample from a particular collection container can be tracked through application of the sample of GM onto the dry solid medium. Moreover, if the robotic system includes a processing system, a sample of GM may be removed from an original collection container, applied to the dry solid medium, and tracked through processing without need for human contact.

Advantages of a kit of the invention include: increased safety to human sample handlers during placement of a sample onto a dry solid medium, decreased human labor costs in applying a sample to the dry solid medium, and decreased chance of sample contamination during handling.

A container for a kit of the invention may be made from any known material. The material of a kit container may be selected based on the type of analysis to be performed on a sample of GM stored on a dry solid medium. Typical materials from which a container of the kit may be prepared includes polystyrene, polypropylene and other materials used in the art. A kit may include a single container with a dry solid medium. Alternatively, a kit may contain as many containers as a robotic or other transferring system can operate with. In a typical embodiment, a kit of the invention may be a plate such as a Corning® 96-well assay plate (Corning Glass Works) or Falcon® 96-well assay plate (Becton Dickenson and Company) with each well of the plate containing a dry solid medium. A multiple container kit such as a multi-well plate may include a different dry solid medium in each container. Thus, for example, a kit may be prepared with a single type of dry solid medium for screening multiple blood samples for a single gene whose primer may be included on the dry solid medium. In another example, a kit may be prepared for screening a single blood sample for multiple genes. Thus, in this example, each container may contain a dry solid medium and each dry solid medium include a different primer.

An example of using a kit with a 96 well container which can be used on a Rosys 3300 II to apply and wash a sample of GM in whole blood follows:

According to this example, each well of a 96 well plate, may include a 2 mm to 5 mm, preferably about a 3 mm diameter, prepunched dry solid medium disc in each of the 96 wells.

A 5 µl sample of whole blood is transferred from a blood collection tube, pre-treated with EDTA, citrate, or heparin, onto a dry solid medium disc in a well, using a new tip for each transfer. If the tubes are labeled with a bar code, and if the robotic system includes a bar code reader, each sample put onto a dry solid medium can be tracked. The plate is incubated to dry the blood sample for about 10 to 20 minutes, preferably about 15 minutes at 45° to 55° C., preferably 50° C. Approximately 200 µl of Gentra One-Step™ (Gentra Systems Inc., Plymouth, Minn.) is added to each well and the plate is incubated for approximately 10 to 20, preferably 15 minutes, at approximately 25° to 30° C., preferably 27° C. This procedure is repeated two times. After the second repeat, the wells are washed two times with approximately 200 µl of 100% isopropanol. A well is then incubated for approximately 10 to 20 minutes, preferably 15 minutes, at about 55° to 65° C., preferably 60° C.

The dry solid medium containing a washed sample of GM in each of the 96 wells may be removed if different subsequent analysis is to be performed on each sample. Alternatively, if all samples are to be subjected to the same subsequent analysis, they may be further processed in the 96 well container.

EXAMPLES

Example 1

In situ PCR Amplification of Blood DNA Stored on Dry Solid Medium

A sample of blood DNA stored on the dry solid medium of the invention was amplified in situ by the polymerase chain reaction (PCR) technique. The dry solid medium used in this Example was cellulose based paper having sorbed thereto a composition comprising, per sq. cm of paper, 2 micromols uric acid, 8 micromols tris (free base), 0.5 micromols EDTA and 1 mg SDS. The stored blood was washed and suitable ions added prior to PCR amplification.

1.1 Single Phase Phenol Wash

A. Materials

Solution A:

Single-phase phenol wash solution. A suitable mixture is phenol, 50 gm containing 120 mg of 8-hydroxyquinoline that has been saturated with 10 ml of 1.0 M tris-acetate pH 8.0 and 1.0 ml 2-mercaptoethanol. After saturation by shaking at room temperature, the aqueous phase is thoroughly removed and discarded.

Solution B:

Aqueous alcohol wash solution. 75% v/v Isopropanol, 25% v/v 0.1M potassium acetate at pH 7.8.

Solution C:

Ionic aqueous wash solution. 75% v/v Isopropanol, 25% v/v 0.01M magnesium acetate.

B. Method

All steps are preferably carried out in a single tube made of a suitable phenol resistant material, e.g. polyethylene.

1. Removal of protein: a 5 mm×5 mm square of blood impregnated dry solid medium was treated with 1 ml of solution A, for approximately 1.5 hours at 45° C. (since no primers were present, this temperature and time is not critical). The solution A was then aspirated to waste and the paper square quickly washed three times with 0.25 ml of solution A. Each wash was for only a few seconds and was immediately aspirated to waste.

2. Removal of phenol and addition of suitable ions: the dry solid medium from step (a) above, was rapidly washed three times with 1 ml of solution B. Washes were at room temperature and were simple additions followed by aspiration to waste. The paper was then washed for 20 minutes at room temperature with solution C. (This is to saturate the GM on the paper with magnesium ions and remove the last of the phenol.) The solution C is aspirated to waste and the dry solid medium was solvent-dried with one wash of pure isopropanol and then vacuum dried.

The washed dry solid medium was relatively quite white without any obvious remnants of the red-brown color of blood. It was then used in a PCR reaction mix.

1.2 Amplification of DNA on Dry Solid Medium

The washed sample on dry solid medium described above has been shown to be a suitable substrate for DNA polymerase chain reaction (PCR) amplification of DNA.

A. Materials

1. Specimens

Extracted DNA: 10 ml of blood was removed from a male volunteer using standard protocols.

Dry solid medium: Blood samples from the same volunteer were applied directly to the dry solid medium with subsequent single phase phenol washing as described above. The dry solid medium was cut into about 1 mm×1 mm pieces for use in PCR reactions.

2. Targets for Amplification

Target No. 1: Region of exon 2 of the n-Ras proto-oncogene on chromosome 1. The primers used are:

R1: 5' TGA CTG AGT ACA AAC TGG TGG TG 3' (SEQ ID NO:1)

R2: 5' CTC TAT GGT GGG ATC ATA TTC A 3' (SEQ ID NO:2).

The amplified DNA fragment obtained with these primers is 110 bp in size.

Target No. 2: A male specific Y chromosome repeat sequence. The primers are:

007: 5' TGG GCT GGA ATG GAA AGG AAT GCA AAC 3' (SEQ ID NO:3) and

008: 5' TCC ATT CGA TTC CAT TTT TTT CGA GAA 3' (SEQ ID NO:4). The amplified DNA fragment obtained with these primers is 124 bp in size.

Target No. 3: A male specific Y chromosome repeat sequence. The primers used are:

004: 5' GAA TGT ATT AGA ATG TAA TGA ACT TTA 3' (SEQ ID NO:5) and

006: 5' TTC CAT TCC ATT CCA TTC CTT TCC TTT 3' (SEQ ID NO:6). The amplified DNA fragment obtained with these primers is 250 bp in size.

B. Method

1. PCR Protocol

Extracted DNA (1 µg) or about 1 mm×1 mm fragments of washed dry solid medium containing a sample of blood DNA were placed into 0.5 ml Eppendorf tubes and made to 25 µl in PCR reaction mixture consisting of:

---

67 mM Tris HCl (pH 8.8 @ 25° C.)
16.6 mM $(NH_4)_2$ $SO_4$
2.0 mM $MgCl_2$
0.01% (w/v) gelatin
0.1 mM deoxynucleotides (dATP, dTTP, dCTP, dGTP)
0.25 µg of each primer (for respective target)
0.25 U of Taq DNA polymerase.

---

2. The amplification conditions

The mixture was overlaid with 25 µl of light mineral oil and DNA amplification was performed by 30 cycles of amplification on a Perkin Elmer-Cetus "thermal cycler". The first cycle consisted of:

| DNA denaturation | 6 min. @ 94° C. |
| Primer-DNA annealing | 1 min. @ 55° C. |
| Taq DNA polymerase extension | 1 min. @ 75° C. | followed by 29 cycles as above except DNA denaturation was for 1 min @ 94° C. and the extension time on the last cycle was 10 min @ 72° C. before cooling the reaction mixture to 4° C.

1.3 Results

After amplification, 10 μl aliquots of PCR mixture were analyzed by electrophoresis on 15% (w/v) polyacrylamide gels. Amplified target DNA was visualized by UV illumination of the ethidium bromide stained gel.

An analysis of the products from PCR amplification of extracted blood DNA and blood DNA stored on dry solid medium are shown in FIG. 1, as follows:

Lanes 1–3: target No. 1, lane 1: 1 μg DNA, lane 2: 1 mm² filter, lane 3: control (no DNA);
Lanes 4–5: target No. 2, lane 4: 1 μg DNA, lane 5: 1 mm² filter; Lane 6: control (no DNA);
Lanes 7–9: target No. 3, lane 7: 1 μg DNA, lane 8: 1 mm² filter, lane 9: control (no DNA);
lane S: DNA size markers (pUC19/HpaII digest).

The results shown in FIG. 1 clearly demonstrate that the DNA has not been changed in any way as a result of its storage on the dry solid medium of the invention, and that it can be used in situ as described herein.

Example 2

PCR Reactions on DNA Stored on Dry Solid Medium Including Primers

PCR analysis was performed on dry solid medium including primers added to the dry solid medium prior to the collection of a sample of blood DNA.

2.1 Genetic Material

A. Materials

1. DNA Templates

For preparing samples of genetic material containing DNA, 3 μl of human blood was applied to a 3 mm square sample of dry solid medium, and the blood was allowed to dry. Unless otherwise indicated, this 3 mm square was then used in each PCR reaction. 3 μl of blood corresponds to approximately 250 nanograms of white-cell DNA. In addition, a control sample of purified human DNA in free solution was amplified using PCR.

2. Primers

Two synthetic oligonucleotide primers derived from the human Class II HLA gene, DQ-alpha, were used in the experiments. Their sequences are:

5' GTGCTGCAGGTGTAAACTTGTACCAG 3' (SEQ ID NO:7)
5' CACGGATCCGGTAGCAGCGGTAGAGTTC 3' (SEQ ID NO:8)

The size of the PCR product expected using the two primers is 262 bp. Each primer was stored as a stock solution at a concentration of 50 ng/ul. When added to the dry solid medium prior to processing, 150 ng of both primers was added to the 3 mm square of dry solid medium. The primers were always used together at equal concentrations.

2.2 Single Phase Phenol Wash

Solution A:

Single-phase phenol solution. 50 g of phenol, containing 120 mg of 8-hydroxyquinoline, was saturated with 10 ml of 1.0 M Tris-acetate pH 8.0 and 1.0 ml of 2-β-mercaptoethanol. After saturation at between 0° C. and 4° C., the aqueous phase was thoroughly removed and discarded.

Solution B:

Aqueous alcohol wash solution. 75% v/v isopropanol, 25% v/v 0.01M potassium acetate, pH 7.8.

Solution C:

Ionic aqueous wash solution. 75% v/v isopropanol, 25% v/v 0.01 M magnesium acetate.

B. Method

1. Washing the Dry Solid Medium

Samples of genetic material stored on the dry solid medium including a primer were processed by first washing the medium with 200 μl of Solution A for two hours at either 37° C. or 50° C., followed by two quick rinses of the aqueous phase with Solution A. The medium was next rinsed three times for five minutes each with 200 μl of Solution B at room temperature. The medium was then washed with 200 μl of Solution C for 20 minutes at room temperature and then dried under vacuum. (The wash times were all in excess. In practice, shorter times may be used. The effectiveness of the washes may be monitored by observing loss of color: (1) the hemoglobin; and (2) the hydroxyquinoline.)

2.3 PCR Protocol

A. Materials

1. The Example PCR Mix 50 μl.

The following mixture was placed on washed dry solid medium containing a sample of blood before heat-cycling:

| 67 mM tris-HC1, (pH 8.8 @ 25° C.) |
| 16.6 mM $(NH_4)_2$ $SO_4$ 0.2 mg/ml gelatin |
| 0.2 mg/ml gelatin |
| 0.45% Triton X-100 |
| 2.0 mM MgCl2 |
| 0.2 mM each of dATP, dTTP, dCTP, dGTP |
| 2.5 units Taq polymerase. |

Template blood DNA was on dry solid medium or purified human DNA as free solution. (50 ng template added when in free solution.)

As shown in table 1, primers were included with the dry solid medium and/or in free solution. (100 ng each primer was if added as free solution.)

B. Methods

1. The Amplification Conditions 4 min. @ 94° C. (start conditions)
1 min. @ 94° C.
40 sec. @ 50° C. (32 cycles)
1 min. @ 72° C.
4° C. (soak-end conditions)

The expected product is a 242 bp segment of the human class-II HLA gene, DQ-alpha.

2. Electrophoresis Conditions

Electrophoresis was in 1% agarose, 0.045 M tris, 0.045 M Boric acid, 1 mM EDTA, pH 8.0, 1.5 hours at 8.5 volts/cm.

C. Results 3 mm×3 mm primer-loaded dry solid medium were taken. 3 μl of freshly collected human blood from one donor was placed on all dry solid medium samples and allowed to dry. It was then stored at room temperature for 7 days.

The squares of dry solid medium were then washed using the single phase phenol wash and all media-squares then dropped into PCR mixes either with or without added primers. There were thus trials in which the primers were added to the medium before loading blood to the medium, after loading blood to the medium, and to the final PCR mix (see Table 1).

After the cycling 8 µl samples of each reaction mix were electrophoresed with Promega PCR marker mix (Promega Corp., Madison, Wis.). (Bands at 1000 bp, 750 bp, 500 bp, 300, 150, 50.) The gel was stained with ethidium bromide and the product bands photographed (see FIG. 2).

Figure 2:
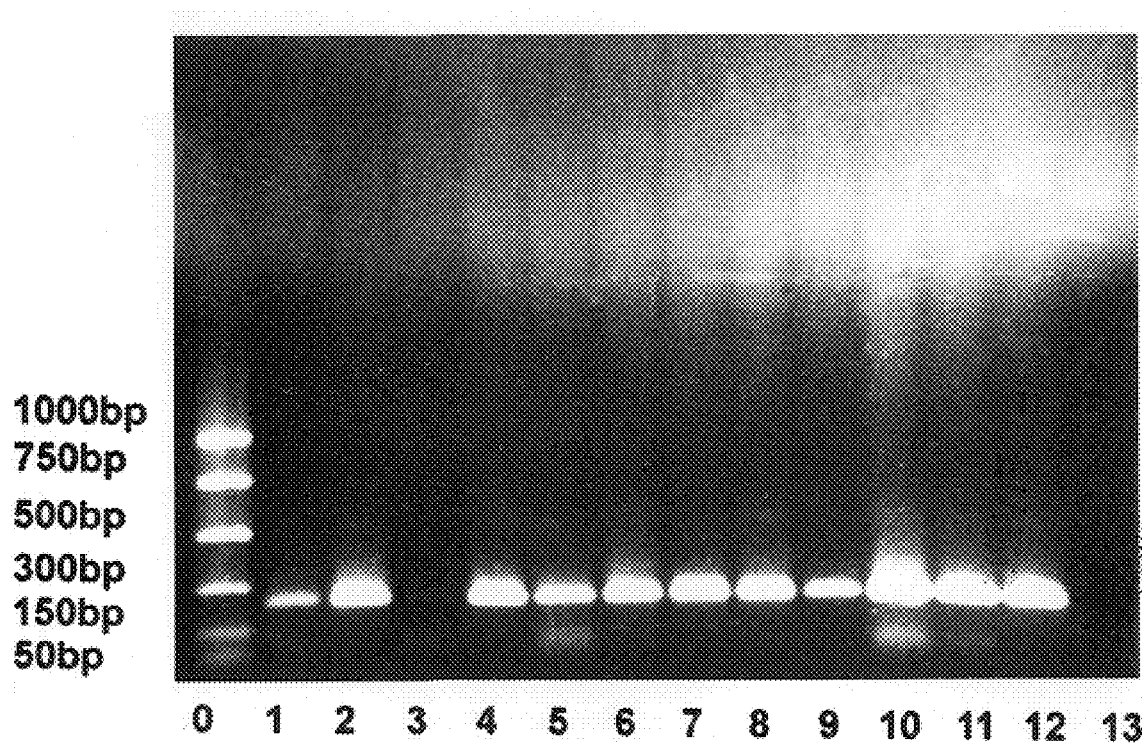
FIG. 2, Photograph of ethidium bromide stained gel of PCR amplified DNA from blood samples stored on a dry solid medium of the invention which included oligonucleotide primers for PCR analysis.

Four samples were processed with the single phase phenol wash taking place at 37° C., and four samples were processed with the single phase phenol wash taking place at 50° C. Subsequent processing steps and PCR reaction conditions for the two sets of samples were identical. FIG. 2 shows that extractions performed at 37° C. generated bands of the predicted size, and whose intensities varied (lanes 1–4), while extractions performed at 50° C. yielded intense bands of the predicted size (lanes 5–8). To show that the PCR products on DNA recovered from the dry solid medium were specific and corresponded to the expected PCR product, PCR reactions were performed on human DNA purified using standard methods (FIG. 2, lane 12), or using no DNA (FIG. 2, lane 13). No product was observed if no exogenous DNA was added to the reaction (FIG. 2, lane 13), and the product obtained with purified DNA comigrated with the PCR product obtained from processed samples of medium (FIG. 2, compare lanes 11 and 12).

Two additional sets of samples were then extracted at 37° C. To one reaction primers were added to the dry solid medium after the blood. To a second reaction primers were likewise added to the dry solid medium after the blood, and additional primers were added just prior to the beginning of the PCR reaction. The results of this experiment are shown in FIG. 2, lanes 9 and 10, respectively. Lane 9 reveals that the DNA on the dry solid medium generated a PCR product of the expected size when primers are added to the dry solid medium after the collection of the blood sample. A more intense PCR product of the expected size was obtained when primers were added just prior to performing the PCR reaction (compare lanes 9 and 10). The results of these experiments are summarized in Table 1.

TABLE 1

Experimental Conditions of PCR Reactions on DNA Stored on Dry Solid Medium

| Source of Template DNA | Time of Addition of Primers | Phenol Wash Temperature | Lanes in FIG. 2 | Mean Results of PCR |
|---|---|---|---|---|
| Human blood on washed dry solid medium | A | 37° C. | 1–4 | ++ |
| Human blood on washed dry solid medium | A | 50° C. | 5–8 | ++++ |
| Human blood on washed dry solid medium | A | 50° C. | 11 | ++++ |
| Purified human DNA in solution | D | N.A. | 12 | ++++ |
| No DNA | D | N.A. | 13 | – |
| Human blood on washed dry solid medium | B | 37° C. | 9 | +++ |
| Human blood on washed dry solid medium | C | 37° C. | 10 | ++++ |

KEY:
A = Primers included on dry solid medium before collection of blood sample.
B = Primers included on dry solid medium after collection of blood on the medium.
C = Primers included on dry solid medium after collection of blood on the dry solid medium, and additional primers added just prior to PCR reaction.

TABLE 1-continued

Experimental Conditions of PCR Reactions on DNA Stored on Dry Solid Medium

| Source of Template DNA | Time of Addition of Primers | Phenol Wash Temperature | Lanes in FIG. 2 | Mean Results of PCR |
|---|---|---|---|---|

D = Primers added just prior to PCR reaction.
N.A. = Not applicable.
++++ = intense bands.
+++ = Moderately intense bands.
++ = Moderate bands.
+ = Weak bands.

In summary, the use of the dry solid medium containing primers is clearly practical, it opens a window of technique that makes large-scale PCR analysis much more practical and amenable to less skilled labor, and opens potential new applications, with unstable templates.

Example 3

In situ Digestion of Stored Blood with Restriction Endonuclease Eco R1

To determine if samples of blood DNA stored on a cellulose-based dry solid medium were digestible in situ with restriction endonucleases, and thus suitable for procedures such as RFLP analysis, samples of blood were collected on cellulose-based dry solid medium, washed with single phase phenol wash and digested with the restriction enzyme Eco R1. In this experiment, samples of blood were stored on the dry solid medium for as long as 18 months prior to processing.

3.1 Single Phase Phenol Wash
  A. Materials and Methods
  The single phase phenol wash and other wash solutions are described in Example 1 and 2. 1.5 ml of solution A was added to a dried 10 mm×10 mm piece of dry solid medium containing approximately 0.1 ml of dried human blood, and the solution was mixed using a standard laboratory mixer and incubated at 37° C. for 30 minutes. The solution A was then removed by aspiration and fresh solution A added. Treatments with solution A were repeated until all the heme color disappeared from the dry solid medium.

Next, the samples were washed five times with solution B for two minutes each, then twice with solution C, also for about two minutes each. Between each wash, the medium sample was subjected to centrifugal stripping. For this the medium was briefly spun in a small microfuge tube in which a hole had been pierced and which had been nested inside a larger microfuge tube. The medium was then dried under vacuum or, alternatively, by centrifugal stripping. Following the processing steps the samples which initially were black after application of the blood and subsequent drying, were white.

3.2 Digestion of Samples Stored on Dry Solid Medium Using Restriction Enzymes
  A. Material
  Restriction enzyme Eco R1 were used in buffers supplied by Boehringer Manheim.
  B. Method
  The washed dry solid medium was moistened with 50 µl of restriction enzyme buffer containing an excess of restriction enzyme. For digestions with the restriction enzyme Eco R1, 60 units of enzyme was added. To ensure complete wetting, the medium was wet in the buffer, centrifugally stripped, and remoistened with the buffer and enzyme mix. Digestions proceeded for 2.5 hours at 37° C.

The restricted DNA was stripped from the medium by first centrifugally stripping the medium and collecting the stripped fluid. DNA was then further removed by washing the solid medium with 25 μl of 7.5M ammonium acetate, followed by a wash with 25 μl of 2.5M ammonium acetate. At each wash step the medium was subjected to centrifugal stripping in order to maximize recovery of the fluids. The fluids from the wash steps were combined in a final volume of about 100 μl. The DNA was precipitated from the collected fluid by adding 250 μl of ethanol, and air-drying the final pellet. The pellet was resuspended in 20 μl of water, and 10 μl of the resuspended pellet was used in gel electrophoresis.

3.3 Gel Electrophoresis

A. Conditions for Gel Electrophoresis

Digestion products were electrophoresed in a 1.5% agarose gel prepared in Tris-Acetate (composition was 0.01M Tris, 0.005M sodium acetate, 0.5M EDTA adjusted to pH 7.8 with acetic acid) at 50 V, 80 mA for 2 hours, after which the gel was stained with ethidium bromide and photographed. (See FIG. 3).

3.4 Results

Figure 3:
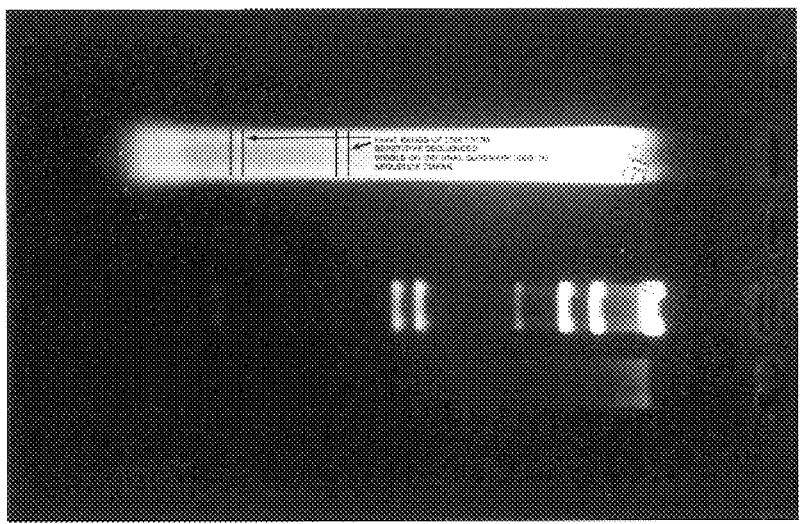
FIG. 3, Photograph of ethidium bromide stained gel of Eco R1 digestion of DNA from human blood stored on the dry solid medium of the invention.

To determine if blood samples stored on media of the invention for extended periods of time could be digested with restriction enzymes, samples of cellulose-based dry solid medium to which blood had been added 19 months previously, 11 months previously, or two weeks previously were processed and then digested with Eco R1. FIG. 3 contains a photograph of the ethidium staining pattern and reveals a smearing pattern characteristic of an Eco R1 digest of human DNA. Thus, DNA stored on the medium for at least 19 months is digestible with restriction endonucleases.

Example 4

Inactivation of Herpes Simplex Virus Type I and other microorganisms, by the Dry Solid Medium In these experiments dry solid medium prepared according to the invention was tested for its ability to inactivate herpes simplex virus, type I (HSV). HSV type I was chosen because it is a relatively resistant to inactivation and is transmissible through blood and other bodily fluids.

4.1 Isolation of HSV Virus

A. Materials and Method

A recent clinical isolate of HSV type I recovered from an eye lesion was grown to high titre ($>10^8$ plaque forming units/ml) in tissue culture flasks of HEp2 epithelial and MRC-5 fibroblast cells, harvested off the flasks, and sonicated to release intracellular virus. Viral particles were concentrated by high-speed centrifugation of a clarified supernatant of the sonicate and were resuspended in viral transport medium (VTM) containing 0.2M sucrose in a 0.02M phosphate buffer (pH 7.6), 10% fetal calf serum, and antibiotics.

4.2 Application of Viral Particles to the Dry Solid Medium and Subsequent Recovery For experiment I, the crude viral preparation was diluted 1:10 in either VTM or in fresh, heparinized blood. A 10 μl sample of the dilution was tested in duplicate on both untreated 10 mm×10 mm pieces of untreated cellulose based paper and also on 10 mm×10 mm square pieces of dry solid medium prepared according to the invention. After application of virus, the squares were supported in air by fine forceps, and after the appropriate time interval, the virus was eluted from the squares by vigorous agitation in 1 ml of MRC-5 maintenance medium (MM) (Eagles MEM based medium with Earle's salts) containing 2% fetal calf serum.

In experiment II, a stock virus was taken from storage at –70° C. and diluted 1:4 in citrated blood.

4.2 Assaying Viral Infectivity

A. Material and Method

The eluate was tested for infectivity using a fluorescent focus assay. Samples were diluted 1:100 in MM, and 0.2 ml of the dilution was then added to a well of MRC-5 fibroblasts in a 48-well cluster tray. After a 45 minute incubation at 37° C., the sample was replaced with 0.5 ml MM and the tray was incubated overnight at 37° C. in the presence of 5% CO2. Cells were then fixed, stained with fluorescein-conjugated antibody to HSV, and the number of fluorescent foci was counted under a reverse-stage fluorescent microscope.

4.3 Results and Discussion

HSV type 1 viral particles were added either to untreated cellulose based paper or to cellulose based paper treated according to the invention to produce the dry solid medium, and then eluted after varying lengths of time. In one experiment, the virus was stored in VTM, and in the second the virus was resuspended in blood. The results of the experiment are shown in Table 2. In both experiments, viral infectivity was reduced to undetectable levels—in these conditions, greater than 99.5% inhibition—when virus was added to the dry solid medium, even when the viral particles were eluted immediately. Viruses in blood eluted from untreated cellulose based paper (CBP), in contrast, were only slightly, if at all, inhibited. A similar inhibitory effect on HSV infectivity was observed when the experiments were performed with viruses recovered from a frozen stock.

The invention has also shown the inhibitory effect of the dry solid medium on growth of *Staphylococcus aureus*, *Staphylococcus epidermidis* and adventitious microorganisms in the environment.

TABLE 2

Infectivity of HSV Following Application on to Untreated cellulose based paper (CBP) Paper or on to Dry Solid Medium

| | A. HSV in VTM | | B. HSV in Blood | |
|---|---|---|---|---|
| Treatment | Viral Titer | Per Cent Inhibition | Viral Titer | Per Cent Inhibition |
| Untreated (virus added directly to MM) | $1.9 \times 10^7$ | 0 | — | |
| Virus spotted on treated CBP and immediately eluted into MM | $<5.0 \times 10^4$ (no virus detected) | >99.5 | $<5 \times 10^4$ (no virus detected) | 99.5 |
| Virus spotted on untreated CBP and immediately eluted into MM | $1.2 \times 10^7$ | 37 | $9.8 \times 10^6$ | 48 |
| Virus spotted on treated CBP and eluted onto MM after 10 minutes | $<5 \times 10^4$ (no virus detected) | >97 | $<5 \times 10^4$ (no virus detected) | >97 |
| Virus spotted on untreated CBP and eluted into MM after 10 minutes | $1.8 \times 10^6$ | 90 | $9.7 \times 10^6$ | 47.5 |

Example 5

Method for treating the dry solid medium of the invention for use in standard analysis systems The dry solid medium of the invention, with or without components for subsequent analysis can also be used in standard assays of analytes for diagnostic purposes, e.g., in the Guthrie Test for phenylketonuria (PKU) and enzymic assays such as a test for galactosemia. Both of these tests are routinely carried out on newborn infants. Prior to analysis using such standard assay systems, it is preferable to neutralize the SDS and EDTA on the dry solid medium containing a sample of blood before the analysis of such analytes by adding a "converter solution".

5.1 Dry Solid Medium Converter Solution

The dry solid medium converter solution works by binding the SDS and EDTA.

A. Materials and Methods

The dry solid medium converter solution includes the following mixture:

1. 577 mg Protamine sulphate (salmine) Sigma No-4380, lot 71F-0037, is added to 7.69 ml water and shaken (to give 75 mg/ml).

This batch will be nominally 75 mg/ml before dialysis. This concentration is near to the solubility of the protamine. It dissolves slowly as a gluey turbid mass.

2. Dialysis: this is a clean-up precaution to assure that the material is essentially sterile and fully dissolved.

The gluey turbid mass is placed in a dialysis bag approx. 1.5 cm in diameter by 2 cm to 10 cm in length. Both ends of the bag are knotted tightly. The bag is then weighed and dropped into a 1 liter flask containing about 800 ml of 50 mM of magnesium acetate with chloroform and a stirring bar. The material is dialyzed in the flask, overnight, against the 800 ml of 50 mM magnesium acetate with an excess of chloroform (approx. 5 ml) present as a sterilizing agent. The protamine almost completely dissolves overnight giving a clear solution and few obvious small lumps of debris.

The weight of the bag increases:

Weight of bag before dialysis =8.1 g 20 hour dialysis, 4° with $CHCl_3$ saturated fluid.

Weight of bag after dialysis=8.67 g.

Thus, the concentration of protamine is now, nominally, 70 mg/ml. (Assuming no losses through bag.)

3. The bag was then punctured at the bottom, and the fluid collected and centrifuged at 4000 rpm (approx. 2000×g) for 10 mins. to remove debris.

4. 1 ml lots were stored at −80° C.

5. Prior to analysis, about 3 ul of the converter solution is applied to each 3 mm diameter disk of dry solid medium containing a sample of blood.

5.2 PKU Screening Procedure (Guthrie Test)

The Guthrie test is based on the stimulatory effect of phenylalanine on the growth of *Bacillus subtilis* in the presence of beta-2-thienylalanine growth inhibitor.

Disks of blood samples stored on the dry solid medium of the invention are placed on agar containing bacterial spores and the inhibitor. Following incubation at 37° C. for 16 to 18 hours, the diameter of the growth around the disk is proportional to the concentration of phenylalanine. Higher than normal levels in infants is indicative of phenylketonuria.

An advantage of using the dry solid medium for the Guthrie test is that the disk of dry solid medium retains proteins and hemoglobin from the sample, leaving a cleaner area around the disk and making the interpretation of the result easier. In fact, samples of blood containing phenylalanine which were stored on the dry solid medium consistently gave at least as strong bacterial growth rings as equivalent samples on standard paper.

Also, because sufficient bacterial spores are used in a Guthrie test and the rate of growth is so fast, the inhibition or killing of bacteria by reagents of the dry solid medium which were proximal to the dry solid medium did not cause a problem for interpreting the results. Therefore, when using the dry solid medium it is not necessary to apply the converter solution to the disk prior to the test. However, it is an advantage to do this to remove an observable weak zone of growth inhibition.

5.3 Screening for Galactosemia

Galactosemia screening requires the use of active enzymes to assay for galactose and galactose phosphate. The main enzyme, beta-galactose dehydrogenase reduces NAD to NADH and this is observed spectrophotometrically.

This assay is severely inhibited by components of the composition of the dry solid medium, but the inhibition can be substantially eliminated by the application of converter solution to a sample of blood stored on the dry solid medium.

After addition of the converter solution, just prior to the enzymic assay, the assay has been observed to perform in the same way as it does with a sample of blood on untreated cellulose based paper. Of course, the dry solid medium has the advantage of providing the benefits of pathogen killing and preservation of the sample compared to standard materials used.

All patents in the specification are indicative of the level of ordinary skill in the art to which this invention pertains. All patents are herein incorporated by reference to the same extent as if each individual patent and publication was specifically and individually indicated by reference.

It will be apparent to one of ordinary skill in the art that many changes and modifications can be made in the invention without departing from the spirit or scope of the appended claims.

What is claimed is:

1. A dry solid medium for storing at least one sample of genetic material, said dry solid medium comprising:
   (a) a solid matrix having sorbed thereto a composition comprising a protein denaturing agent;
   (b) a component for subsequent analysis of said sample of genetic material; and
   (c) a retaining agent for retaining said component for subsequent analysis on said solid matrix, wherein said retaining agent comprises a hydrophilic solid carrier in wax and wherein said hydrophilic solid carrier comprises a starch, cellulose or cotton material.

2. The dry solid medium according to claim 1, wherein said protein denaturing agent is a detergent.

3. The dry solid medium according to claim 1, wherein said sample of genetic material stored on said dry solid medium is RNA.

4. The dry solid medium according to claim 1, wherein said sample of genetic material stored on said dry solid medium is blood DNA.

5. The dry solid medium according to claim 1, wherein said component for subsequent analysis of said sample of genetic material is a nucleotide sequence.

6. The dry solid medium according to claim 1, wherein said component for subsequent analysis of said sample of genetic material is a target sequence stabilizer.

7. The dry solid medium according to claim 1, wherein said retaining agent reduces loss of said component for subsequent analysis during an aqueous wash procedure.

8. The dry solid medium according to claim 1, wherein said component for subsequent analysis of said sample of genetic material is applied to said dry solid medium after said sample of genetic material is applied to said dry solid medium.

9. The dry solid medium according to claim 1, wherein said dry solid medium is a card comprising more than one component for subsequent analysis.

10. The dry solid medium according to claim 1, wherein said composition of said dry solid medium further comprises a free radical trap.

11. The dry solid medium according to claim 2, wherein said detergent is an anionic detergent.

12. A method for storing and subsequent analysis of a sample of genetic material comprising:
   (a) applying a sample of genetic material to a dry solid medium, said dry solid medium comprising:
      (i) a solid matrix having sorbed thereto a composition comprising a protein denaturing agent;
      (ii) a component for subsequent analysis of said sample of genetic material; and
      (iii) a retaining agent for retaining said component for subsequent analysis on said matrix, wherein said retaining agent comprises a hydrophilic solid carrier in wax and wherein said hydrophilic solid carrier comprises a starch, cellulose or cotton material;
   (b) storing said sample of genetic material;
   (c) washing said sample of genetic material; and
   (d) analyzing said sample of genetic material.

13. The method according to claim 12, wherein any of said steps (a), (b), (c) and (d) are performed on an automated system.

14. The method according to claim 12, wherein said sample of genetic material analyzed is RNA which is first transcribed to DNA using reverse transcriptase initiated polymerase chain reaction.

15. The method according to claim 12, wherein said sample of genetic material of step (d) is analyzed using polymerase chain reaction.

16. The method according to claim 12, wherein said washing of said sample of genetic material of step (c) is performed using an aqueous wash system.

17. A method for storing a sample of genetic material comprising:
   (a) applying a sample of genetic material to a dry solid medium, said dry solid medium comprising:
      (i) a solid matrix having sorbed thereto a composition comprising a protein denaturing agent;
      (ii) a component for subsequent analysis of said sample of genetic material; and
      (iii) a retaining agent for retaining said component for subsequent analysis on said solid matrix, wherein said retaining agent comprises a hydrophilic solid carrier in wax and wherein said hydrophilic solid carrier comprises a starch, cellulose or cotton material; and
   (b) storing said sample of genetic material.

* * * * *